United States Patent [19]

Spademan

[11] Patent Number: 5,183,036
[45] Date of Patent: Feb. 2, 1993

[54] WALKER BRACE

[76] Inventor: Richard G. Spademan, 2600 Capitol Ave. #405, Sacramento, Calif. 95816

[21] Appl. No.: 408,653

[22] Filed: Sep. 18, 1989

[51] Int. Cl.$^5$ ............................................. A61F 5/04
[52] U.S. Cl. ...................................... 602/10; 602/23; 602/27
[58] Field of Search ...................... 128/84 R, 83, 83.5, 128/88, 80 H, 80 R, 80 F, 84 C, 80 DB, 80 D, 80 C, 87 R, 166, 252, 599

[56] References Cited

U.S. PATENT DOCUMENTS

| | | | |
|---|---|---|---|
| 2,206,234 | 7/1940 | Murray | 128/83.5 |
| 2,512,826 | 6/1950 | Clark | 128/80F |
| 2,516,872 | 8/1950 | Hauser | 128/80 H |
| 2,525,658 | 10/1950 | Dumelin | 128/80 H |
| 2,591,373 | 4/1952 | Petruch | 128/80 F |
| 2,594,227 | 4/1952 | Smith | 128/80 F |
| 2,883,982 | 4/1959 | Rainey | 128/80 F |
| 3,481,332 | 12/1969 | Arnold | 128/80 R |
| 4,244,359 | 1/1981 | Dietrich | 128/81 R |
| 4,393,876 | 7/1983 | Dietrich | 128/583 |
| 4,428,369 | 1/1984 | Peckham et al. | 128/80 C |
| 4,649,906 | 3/1987 | Spademan | 128/80 |
| 4,771,768 | 9/1988 | Crispin | 128/88 |
| 4,771,769 | 9/1988 | Crispin | 128/88 |
| 4,856,500 | 8/1989 | Spademan | 128/88 |

FOREIGN PATENT DOCUMENTS

| | | |
|---|---|---|
| 332074 | 12/1984 | Fed. Rep. of Germany . |
| 2122846 | 9/1972 | France . |
| 1213855 | 11/1970 | United Kingdom . |

OTHER PUBLICATIONS

Supplementary European Search Report EP 88 90 5562 of Jan. 22, 1990.

*Primary Examiner*—Robert A. Hafer
*Assistant Examiner*—Michael Brown
*Attorney, Agent, or Firm*—Townsend and Townsend

[57] ABSTRACT

A walker brace for temporary tightening from a close fit position during the support surface contact phase of gait when the patient'weight is applied to the sole to stabilize the leg, ankle and foot from undesirable movement. A leg support assembly (2) of the brace has multiple straps (15, 16) connected to an arm (4) for nesting the leg. A foot support assembly (3) has multiple straps (31, 32) connected to a foot support shell (28) for nesting the foot. An arm (5) is connected to the foot support shell (28) and articulates relative to the arm (4) at a controlled motion ankle hinge (6). A leg strap tightening mechanism (18) includes a tightening rod (20) and a cable (22) for progressive and differential tightening of the straps (15, 16) to stabilize the leg. A foot strap tightening mechanism (44) includes a buckle loop (34) and a cable (41) for tightening of the instep strap (32) to stabilize the foot. The cables (22, 41) pass through foot support shell (28) and a rocker bottom sole shell (29) pivoted at the foot support shell (28). A relative shortening of the cables (22, 41) occurs when the rocker bottom sole shell (29) is pivoted upwardly relative to the foot support shell (28) during the period of time that the patient's weight is applied to the sole.

24 Claims, 1 Drawing Sheet

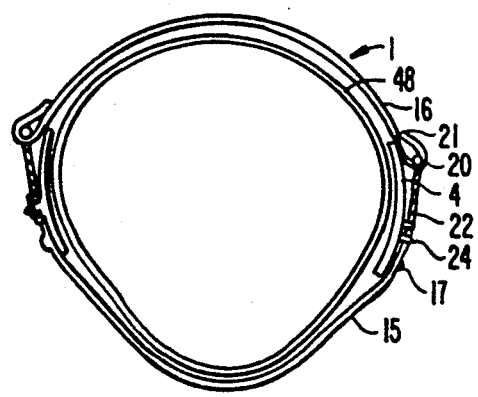
FIG._2.
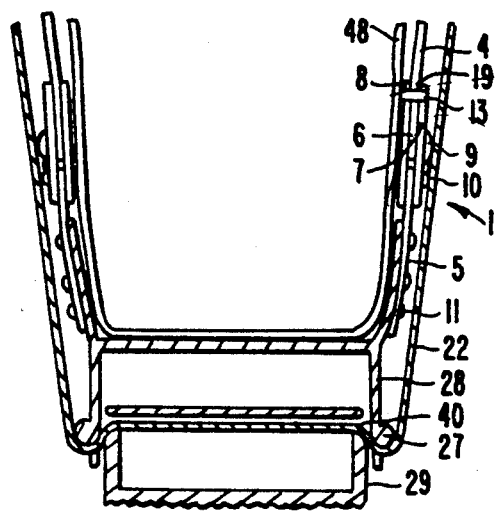
FIG._3.
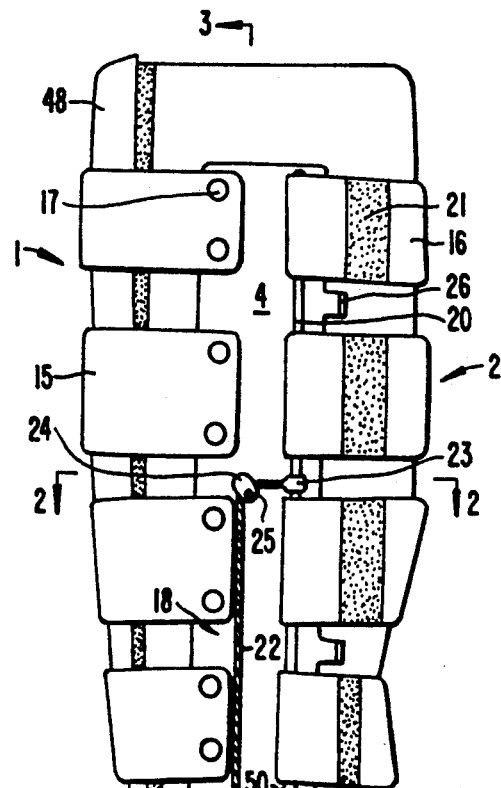
FIG._1.

WALKER BRACE

BACKGROUND OF THE INVENTION

The present invention relates to therapeutic and prophylactic devices, particularly to a walker brace which dynamically temporarily tightens from a snug close fit position on a patient's nested limb to stabilize the leg, ankle and foot from undesirable movement when the patient's weight is applied to the sole during contact loading with a support surface.

Various devices are known such as casts, braces, cuffs and splints that are designed to protect and stabilize the leg, ankle and foot ligaments, tendons and bones as they heal following injury or surgery. Unfortunately, these devices do not provide efficient function during the destabilizing loading phase of walking when the walker brace sole contacts the walking surface. These devices tend to be either too loose on the leg, ankle and foot in which case they do not adequately stabilize the leg, ankle and foot against undesirable or abnormal movement or these devices are held too tightly, intensifying discomfort, prolonging immobility and aggravating the problem of stasis and atrophy.

SUMMARY OF THE INVENTION

It is accordingly a primary object of this invention to provide a walker brace that overcomes the deficiencies of previously known devices of the above known type.

Another object of the present invention is to provide a walker brace that dynamically temporarily tightens on a leg and foot from the snug close fit position to stabilize the leg, ankle and foot in response to loading of the lower extremity when the patient's weight is applied to the walker brace sole during the support surface contact phase of gait.

Still another object of the present invention is to provide a walker brace that can be adjusted to control the amount of tightening from the snug close fit position on the leg and foot to stabilize the ankle in response to loading when the patient's weight is applied to the sole during the support surface contact phase of gait.

Still another object of the present invention is to provide a walker brace that can progressively and differentially tighten on the leg in response to loading during the period of time that the patient's weight is applied to the sole.

BRIEF DESCRIPTION OF THE DRAWINGS

In the drawings:

FIG. 1 is a side elevation view showing a walker brace constructed according to the present invention;

FIG. 2 is a cross sectional view taken along line 2—2 of FIG. 1 showing part of the walker brace assembly secured to the leg: and FIG. 3 is a partial cross sectional view taken along line 3—3 in FIG. 1 showing part of the mechanism used to dynamically tighten the walker brace on the leg.

DESCRIPTION OF THE PREFERRED EMBODIMENT

Referring to FIGS. 1-3, a walker brace 1 for a lower extremity is shown. There is particularly shown in FIG. 1 a walker brace 1 which includes a leg support assembly 2 and a foot support assembly 3 which are respectively connected to a controlled motion hinge assembly 6 at the ankle and which are located on the medial and lateral sides of the leg, ankle and foot. These components comprise a fitting assembly and are respectively adapted to engage the corresponding leg and foot above and below the ankle articulation.

On the medial side of the leg there are upper and lower arms 4 and 5 that are attached to and extend toward each other from the leg support assembly 2 and the foot support assembly 3 respectively. The upper arm 4 and the lower arm 5 terminate at the controlled motion hinge assembly 6. Upper and lower arms 4 and 5 are constructed of substantially rigid material such as plastic or metal. Hinge assembly 6 comprises identical outer and inner hinge plates 7 and 8 which are connected to the lower arm 5 by hinge assembly rivets 10 or the like. Lower arm 5 is connected to a foot support shell 28 of foot support assembly 3 with lower arm rivets 11 or the like. Upper arm 4 is pivotally connected to hinge assembly 6 by means of a hinge bolt 9 which passes through a bore in the outer hinge plate 7, the upper arm 4 and the inner hinge plate 8. Hinge assembly 6 further includes a stop pin 12 operatively coupled with the hinge assembly and the leg support assembly which can be press fit into one of a series of stop pin bores 13 in the outer hinge plate 7 and inner hinge plate 8 coincident with upper arm 4 stop pin bores 13 for controlling the forward and rearward motion of the leg support assembly relative to the hinge and foot support assemblies. Alternatively, a more complex orthotic joint can be used.

Thus, the leg support assembly 2 and foot support assembly 3 articulate at hinge bolt 9. Hinge bolt 9 forms a pivot axis which is substantially perpendicular to arms 4 and 5 and which coincides with the predominant axis through which the leg and foot articulate at the ankle.

The walker brace 1 comprises a leg support assembly 2 surrounding the leg forming a cuff and a foot support assembly 3 surrounding the foot and forming a boot. The leg support assembly 2 includes multiple anterior straps 15 which pass around the anterior aspect of the leg and are secured to the upper arm 4 by snap closures, adjustable velcro ® strips, strap rivets 17 or the like. Multiple posterior straps 16 pass around the posterior aspect of the leg and around a substantially rigid metal tightening rod member 20 and are secured to themselves by the use of velcro ® strip assemblies 21 or the like. The strap and tightening rod member can be located on the anterior aspect of the leg. The tightening rod member 20 can be optionally fixed to upper arm 4 to pivot relative to leg support assembly 2 near the ankle hinge assembly 6 by a tightening rod bolt 50. Also included in the upper arm 4 are tightening rod stops 26 for limiting posterior movement of the tightening rod member 20.

The posterior straps are connected with a leg strap tightening mechanism 18 for tightening against the leg when the patient's weight is applied to the sole. The leg strap tightening mechanism 18 includes the tightening rod member 20, a cable 22 which is connected to the tightening rod member 20 by a cable clamp 23 or the like and then passes around cable guide 24 secured to the upper arm 4 by a cable guide rivet 25 or the like. The cable 22 is then directed toward the foot support assembly 3. The cable 22 passes through an upper arm guide 19 and around bore guide 27 in the foot support shell 28 sidewall, through rocker bottom sole sidewall bore 40 in rocker bottom sole shell 29 to a like leg strap tightening mechanism on the lateral side of the leg. Thus, there is also formed an actuating system operatively coupled with the tightening mechanism and connected with the sole and movable relative to the sole when the patient's weight is applied to the sole.

The foot support assembly 3 includes a plastic or the like, substantially rigid, longitudinally directed, in cross-section (FIG. 3) generally H shaped, snug fitting foot support shell 28, which provides a nest for the foot connected to a sole comprising a substantially rigid, in cross-section (FIG. 3) generally U shaped, curved rocker bottom sole shell 29 pivoted to the foot support shell 28 by rocker bottom sole pivot bolt 30. The pivot bolt 30 can be located near the forefoot and passes through a bore in the foot support shell 28 side wall and the rocker bottom sole shell 29 side wall and allows the rocker bottom sole shell 29 to pivot in an upward and downward direction about the pivot bolt 30. The foot support shell 28 may include a soft footbed insole and the rocker bottom sole shell 29 may have a skid resistant bottom covering, not shown.

The foot support assembly 3 further includes a forefoot strap 31 and an instep strap 32 respectively that pass around buckle loops 33 and 34 and can be adjusted to secure to themselves by the use of velcro ® strip 35 and 36 assemblies, or the like. Buckle loop 33 is connected to the foot support shell 28 by a clasp 37 and a clasp rivet 38 or the like. Instep strap 32 is connected with a foot strap tightening mechanism 44 for tightening against the foot when the patient's weight is applied to the sole. The foot strap tightening mechanism 44 includes buckle loop 34 and a cable 41 which is connected to the buckle loop 34 by a cable clamp 42 or the like and is then directed in a downward direction and passes around bore guide 43 in the foot support shell 28 side wall, through rocker bottom sole side wall bore 47 in the rocker bottom sole shell 29 side wall to a like foot strap tightening mechanism on the lateral side of the foot. Thus, there is also formed an actuating system operatively coupled with the tightening mechanism and connected with the sole and movable relative to the sole when the patient's weight is applied to the sole.

A pivot stop pin 45 can be press fit into one of multiple foot support shell 28 pivot stop bores 46 near the heel in the wall of the foot support shell 28 to control the travel distance of the rocker bottom sole shell 29 and therefore, the travel distance of the actuating system and the amount of tightening of the straps.

The walker brace 1 can also include a soft flexible sleeve 48 wrapped around the leg and foot with a continuous overlapping front region interior of the leg support assembly 2 and foot support assembly 3. An extension spring 49 can be connected to the foot support shell 28 and rocker bottom sole shell 29 to return the rocker bottom sole shell 29 to the unweighted position when there is no contact loading with a support surface.

In use, the walker brace 1 is placed on the wearer's limb by wrapping the soft flexible sleeve 48 around the limb and situating the foot in the foot support assembly 3 and the leg in the leg support assembly 2. The posterior straps 16, forefoot strap 31 and instep strap 32 are tightened snugly around the limb in the unweighted resting position and passed around the tightening rod member 20 and buckle loops 33 and 34 respectively and secured to themselves with the velcro ® strip assemblies 21, 35 and 36. Thus, the walker brace has a close comfortable fit in the resting unweighted position.

The stop pin 12 is press fit into a selected one of stop pin bores 13 that pass through the upper arm 4 for maintaining the selected angle of ankle dorsiflexion, such as is indicated during the early and mid phase of healing of an ankle fracture or ligament sprain. If controlled ankle motion is indicated, such as during the late phase of healing to mobilize the ankle, one or more stop pins 12 are press fit into stop pin bores 13 that do not pass through the upper arm 4, providing an end stop. The pivot stop pin 45 may be press fit into a selected one of stop pin pivot bores 46 to limit the amount of tightening of the straps.

During the period of time that the patient's weight is applied to the sole, when the walker brace rocker bottom sole shell 29 contacts the walking surface, the rocker bottom sole shell 29 pivots in an upward direction about pivot bolt 30. There is relative shortening of cable 22 and cable 41 respectively due to the increased distance between bore guide 27 in the foot support shell 28 and rocker bottom sole side wall bore 40 and bore guide 43 in the foot support shell 28 and rocker bottom sole side wall bore 47. This actuating system results in progressive and differential tightening of the multiple posterior straps 16 on the leg, increasing stability and improving venous return as the tightening rod 20 is pivoted about tightening rod bolt 50 and tightening of the instep strap 32 as the instep buckle loop 34 changes position. Thus, there is dynamic temporary tightening of the leg support assembly 2 and foot support assembly 3 from a snug close fit position on the wearer's nested limb to stabilize the leg, ankle and foot from undesirable movement.

Details have been disclosed to illustrate the invention in a preferred embodiment of which adaptations and modifications within the spirit and scope of the invention will occur to those skilled in the Art. The scope of the invention is limited only by the following claims.

What is claimed is:

1. A walker brace comprising:
   a foot support assembly for receiving a patient's foot including a sole;
   a leg support assembly for receiving the patient's corresponding leg including at least one strap member for tightening against the leg;
   an actuating system coupled with the sole and movable relative to the sole in response to the application of the patient's weight to the sole; and
   a tightening mechanism operatively coupled with the actuating system and the strap member for increasing the tightness of the strap member on the leg in response to movement of the actuating system relative to the sole as a result of the application of the patient's weight to the sole.

2. A walker brace according to claim 1 further comprising at least one strap member included with the foot support assembly for tightening against the foot and a tightening mechanism operatively coupled with the actuating system and the strap member for increasing the tightness of the strap member on the foot in response to said movement of the actuating system.

3. A walker brace according to claims 1 or 2 further comprising an assembly for adjusting the tightness of the strap member.

4. A walker brace according to claims 1 or 2 further comprising an actuating system movable between an unweighted position and a weighted position, and a return member operatively connected with the sole and the actuating system for returning of the actuating system to the unweighted position.

5. A walker brace according to claim 4 further comprising a spring return member.

6. A walker brace according to claims 1 or 2 further comprising a stop member operatively coupled with the sole and the actuating system for controlling the travel distance of the actuating system.

7. A walker brace according to claims 1 or 2 further comprising a tightening mechanism that includes a cable operatively coupled with the actuating system and the strap member.

8. A walker brace according to claims 1 or 2 further comprising multiple strap members and a tightening mechanism for progressive tightening of the strap members.

9. A walker brace according to claims 1 or 2 further comprising an assembly for connecting the foot support assembly to the leg support assembly.

10. A walker brace according to claim 1 further comprising multiple strap members and a tightening mechanism for differential tightening of the strap members.

11. A walker brace according to claim 10 further comprising a tightening mechanism that includes a member that pivots relative to the leg support assembly.

12. A walker brace according to claim 11 further comprising a rod member partially fixed to the leg assembly.

13. A walker brace according to claim 9 further comprising a hinge assembly for connecting the foot support assembly to the leg support assembly.

14. A walker brace according to claim 13 further comprising a controlled motion hinge assembly.

15. A walker brace according to claim 14 further comprising at least one step pin operatively coupled with the hinge assembly and the leg support assembly for controlling the forward and rearward motion of the leg support assembly relative to the hinge assembly.

16. A walker brace according to claim 1 wherein the tightening mechanism is operative coupled to and temporarily increases the tightness with which the first and second strap members engage the foot and leg for as long as the patient's weight is applied to the sole.

17. A walker brace according to claim 1 wherein the actuating system is movable relative to the sole between an un position and a weighted position, and including a return member operatively coupled with the sole and the actuating system for returning the actuating system to its un position.

18. A walker brace according to claim 17 wherein the return member comprises a spring.

19. A walker brace for stabilizing a patient's ankle comprising:
a substantially rigid foot support assembly for receiving the patient's corresponding leg and including at least one strap member for tightening against the foot:
a substantially rigid leg support assembly for receiving the patient's corresponding leg and including at least one strap member for tightening against the leg;
a controlled motion hinge assembly connecting the foot support assembly to the leg support assembly;
an actuating system coupled with the sole and moveable relative to the sole in response to the application of the patient's weight to the sole: and
a tightening mechanism operatively coupled with the actuating system and at least one strap member for increasing the tightness of the strap member on the foot and/or leg in response to movement of the actuating system relative to the sole as a result of the application of the patient's weight to the sole.

20. A walker brace according to claim 19 further comprising at least one stop pin operatively coupled With the hinge assembly and the leg support assembly for controlling the forward and rearward motion of the leg support assembly relative to the hinge assembly.

21. A walker brace for immobilizing an ankle joint between a patient's foot and leg and for increasing the tightness with which the brace is applied when the patient applies his weight to the brace, the brace comprising:
a boot including a substantially rigid support surface for the foot and a foot strap adapted to be placed over an instep portion of the foot;
a substantially rigid cuff substantially immovably secured to the boot, extending from the boot in a general upward direction, and including a leg strap for placement about the leg;
a sole mounted to the boot, formed and positioned so that the sole engages a ground surface when the patient applies his weight to the support surface of the boot and means permitting movement of the sole relative to the rigid support surface when the patient applies his weight to the boot and the sole; and
cable means having ends attached to ends of the foot strap and the leg strap and an intermediate portion in simultaneous engagement with a section of the boot and the sole so that relative movement of the sole under the weight applied thereto by the patient draws the foot strap and the leg strap against the foot and the leg, respectively, with an increased force to thereby temporarily increase the tightness with which the brace engages the foot and the leg in response to and while the patient's weight is applied to the sole.

22. A walker brace according to claim 21, including means for limiting the extent to which the sole can move relative to the boot when the patient's weight is applied to the sole.

23. A walker brace according to claim 22 wherein the movement limiting means includes means for adjusting the amount of relative movement of the sole.

24. A walker brace according to claim 22 including means between the boot and the cuff for varying the angular inclination therebetween.

* * * * *